United States Patent
Zemlok et al.

(10) Patent No.: US 9,610,412 B2
(45) Date of Patent: Apr. 4, 2017

(54) INTERNALLY PRESSURIZED MEDICAL DEVICES

(75) Inventors: Michael Zemlok, Prospect, CT (US); Russell Pribanic, Roxbury, CT (US); Adam Ross, Prospect, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 703 days.

(21) Appl. No.: 13/020,354

(22) Filed: Feb. 3, 2011

(65) Prior Publication Data
US 2011/0218484 A1 Sep. 8, 2011

Related U.S. Application Data

(60) Provisional application No. 61/309,606, filed on Mar. 2, 2010.

(51) Int. Cl.
*A61M 13/00* (2006.01)
*A61B 17/072* (2006.01)
*A61B 17/34* (2006.01)

(52) U.S. Cl.
CPC ....... *A61M 13/00* (2013.01); *A61B 17/07207* (2013.01); *A61B 17/34* (2013.01)

(58) Field of Classification Search
CPC ............ A61M 2005/006; A61M 13/00; A61M 13/003; A61M 13/006; A61M 2202/0225; A61M 2205/3344; A61M 2202/02; A61M 2205/3331; A61M 2210/1021; A61M 2202/0208; A61M 2202/0007; A61M 2202/025; A61M 2202/0275;
(Continued)

(56) References Cited

U.S. PATENT DOCUMENTS 5,328,458 A * 7/1994 Sekino et al. .................. 604/23
5,350,355 A * 9/1994 Sklar ............................... 604/23
(Continued)

FOREIGN PATENT DOCUMENTS

WO 2008157654 A2 12/2008

OTHER PUBLICATIONS

European Search Report dated Apr. 14, 2014 in European Application No. 11 25 0229.
(Continued)

*Primary Examiner* — Bhisma Mehta
*Assistant Examiner* — Laura Schell

(57) ABSTRACT

There are provided pressurized surgical instruments for use in pressurized surgical environments. The pressurized surgical instruments include pressurizing systems for maintaining a neutral or positive pressure flow within the surgical instrument during use. The pressurizing systems include a primary sensor for detecting the pressure of the surgical environment and a pressurizing mechanism for balancing the pressure of the surgical instrument with the surgical environment. The pressurizing mechanism includes a controller to receive and compare the signal sent from the primary sensor to the ambient or internal instrument pressure and a pressure delivery system to provide positive pressure to the interior of the surgical instrument in response to a signal received from the controller. The sources of pressure for the pressure delivery systems may be external or self contained within the surgical instrument.

23 Claims, 13 Drawing Sheets

(58) Field of Classification Search
CPC .. A61M 2202/0216; A61M 2202/0233; A61M 2202/0266; A61M 2205/362; A61M 5/168; A61M 5/16804; A61M 5/16854; A61M 5/16859; A61M 5/172; A61M 5/1723; A61B 17/3474

USPC .................................................. 604/26, 25

See application file for complete search history.

(56) References Cited

U.S. PATENT DOCUMENTS

| | | | |
|---|---|---|---|
| 5,630,783 A * | 5/1997 | Steinberg | A61B 1/015 600/158 |
| 6,206,878 B1 * | 3/2001 | Bishop | A61B 18/042 219/121.55 |
| 6,299,592 B1 | 10/2001 | Zander | |
| 7,833,222 B2 | 11/2010 | Sartor et al. | |
| 7,988,656 B2 * | 8/2011 | Uesugi et al. | 604/23 |
| 2005/0234391 A1 | 10/2005 | Uesugi et al. | |
| 2006/0069306 A1 * | 3/2006 | Banik | A61B 1/00068 600/118 |
| 2007/0088275 A1 * | 4/2007 | Stearns et al. | 604/164.01 |
| 2007/0187453 A1 * | 8/2007 | Smith | A61B 17/07207 227/175.1 |
| 2007/0191759 A1 * | 8/2007 | Stoller et al. | 604/22 |
| 2009/0054893 A1 * | 2/2009 | Sartor | A61B 18/042 606/41 |
| 2009/0137943 A1 | 5/2009 | Stearns et al. | |
| 2009/0270818 A1 | 10/2009 | Duke | |
| 2010/0100094 A1 * | 4/2010 | Truckai | A61B 18/042 606/39 |
| 2010/0168520 A1 * | 7/2010 | Poll | A61B 1/00091 600/169 |
| 2010/0185139 A1 * | 7/2010 | Stearns et al. | 604/26 |
| 2010/0268153 A1 | 10/2010 | Mantell | |
| 2010/0274178 A1 * | 10/2010 | Lepivert | A61B 18/02 604/21 |
| 2011/0054454 A1 * | 3/2011 | Rooks | A61B 18/042 606/27 |

OTHER PUBLICATIONS

Australian Examination Report dated Aug. 19, 2015, issued in Australian Application No. 2014218356.
Chinese Office Action dated Dec. 24, 2015, issued in Chinese Application No. 201110051884.
Canadian Office Action dated Oct. 20, 2016, issued in Canadian Application No. 2,730,864.

* cited by examiner

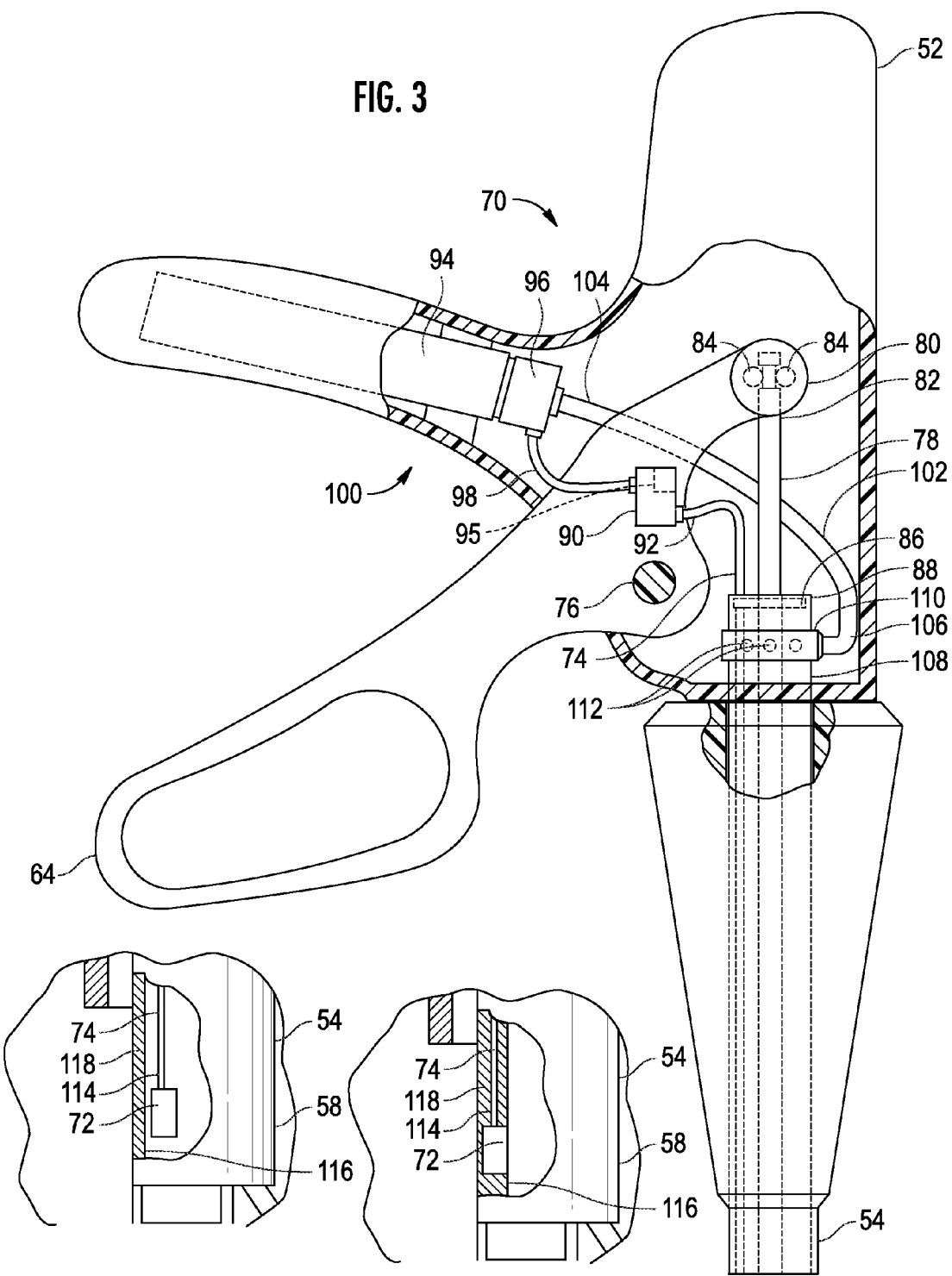

INTERNALLY PRESSURIZED MEDICAL DEVICES

CROSS-REFERENCE TO RELATED APPLICATIONS

This application claims priority to, and the benefit of, U.S. Provisional Patent Application No. 61/309,606, filed Mar. 2, 2010, the entire contents of which are incorporated herein by reference.

BACKGROUND

1. Technical Field

The present disclosure relates to pressurized surgical instruments. More particularly, the present disclosure relates to pressurized surgical instruments incorporating pressurization mechanisms configured to internally balance or exceed pressures detected within an insufflated body cavity.

2. Background of Related Art

During certain surgical procedures, such as, for example, laparoscopic procedures, it is often necessary to separate a body wall of a patient from the underlying tissues in order to create a working space for the surgical instruments. This is typically accomplished by forming an incision through the body wall and inserting an access port or cannula through the incision. A source of expansion or insufflation fluids or gases is provided. The gases are forced through the cannula and into the body cavity. As the insufflation fluids enter the body cavity, the fluids force the body wall away from the underlying tissues to create the working space. This results in the working space having a higher internal pressure than that of the ambient pressure external to the body.

Once the insufflated working space has been created, surgical instruments may be inserted through the cannula and into the insufflated body cavity to perform surgical procedures. These surgical instruments typically include a handle or body portion which remains external to the patient's body and an elongate tubular member having a working instrument or end effector which is inserted through the cannula and into the pressurized body cavity. Since the body cavity is at a higher pressure than that external to the body cavity, insufflation fluids tend to escape up through the elongate tubular member and exit through gaps in the body portion of the surgical instrument. This escape and flow of insufflation gases through the elongate tubular member creates a drawing or siphoning effect within the elongate tubular member which pulls bodily fluids and tissues through the end effectors and into the elongate tubular member. The introduction of bodily fluids and tissues into the end effector and the remainder of the surgical instrument contaminates and may clog the working components of the surgical instrument. This results in difficulty in operating the surgical instrument in addition to contaminants being passed through the surgical instrument.

Therefore, it is desirable to provide a surgical instrument which prevents the escape of bodily fluids and tissues through the surgical instrument. It is further desirable to provide a surgical instrument which incorporates a pressurization mechanism to balance the pressures within the surgical instrument with the pressures within the body cavity in order to prevent escape of the insufflation fluids through the surgical instrument. It is still further desirable to provide a pressurized surgical instrument which can be utilized to augment the insufflation fluids provided by the cannula into the body cavity.

SUMMARY

There is disclosed a pressurized surgical instrument having a body portion and an elongate tubular member extending from the body portion. A primary sensor is positioned within the surgical instrument for detecting a pressure in a working environment. The pressurized surgical instrument additionally includes a pressurization mechanism positioned within the body portion of the surgical instrument for balancing the pressure of the surgical instrument with the working environment. The pressurization mechanism includes a controller connected to the primary sensor and a pressure delivery system connected to the controller. The pressure delivery system provides positive pressure to the interior of the surgical instrument in response to a signal received from the controller and is in fluid communication with an interior of the surgical instrument. Specifically, the pressure delivery system is in fluid communication with an interior of the elongate tubular member The controller incorporates a second sensor for detecting a pressure within the surgical instrument. The controller compares the pressure in the working environment with the pressure within the surgical instrument.

The pressure delivery system includes a tube and a distal end of the tube is connected to a collar in fluid communication with a proximal end of the elongate tubular member. The collar is in fluid communication with the proximal end of the elongate tubular member through a series of ports positioned about the collar.

The primary sensor is positioned within the elongate tubular member. Specifically, the primary sensor is positioned adjacent a distal end of the elongate tubular member. The primary sensor is connected to the controller through a sensor cable. In a particular embodiment, the primary sensor and sensor cable are contained within a wall of the elongate tubular member.

In one embodiment, the pressure delivery system includes a self-contained gas cartridge positioned within the body portion of the surgical instrument. The pressure delivery system includes a valve connected to the self-contained gas cartridge and to the controller such that the valve regulates gas released by the self-contained gas cartridge in response to a signal received from the controller.

In an alternative embodiment, the pressure delivery system includes a pressurizing pump in fluid communication with the interior of the elongate tubular member and connected to the controller. A draw tube extends from the pressurized pump to a location and external of the body portion to draw low-pressure insufflation gases into the pump.

In a further alternative embodiment, the pressure delivery system includes a valve and a connection tube extending from the valve to a connection fitting. The valve is connected to the controller. In this embodiment, the connection fitting is releasably attachable to an external source of insufflation fluids.

DESCRIPTION OF THE DRAWINGS

Various embodiments of the presently disclosed pressurized surgical instruments are disclosed herein with reference to the drawings, wherein:

FIG. 3 is an enlarged area of detail view of FIG. 2 illustrating a self-contained pressurization mechanism located within a handle or body portion of the pressurized surgical instrument;

FIG. 4A is an enlarged area of detail view of FIG. 2 illustrating a primary sensor positioned adjacent a distal end of an elongate tubular member of the pressurized surgical instrument; FIG. 4B is an enlarged area of detail view of FIG. 2 illustrating a primary sensor positioned within a wall of the elongate tubular member of the pressurized surgical instrument;

DETAILED DESCRIPTION OF EMBODIMENTS

Embodiments of the presently disclosed pressurized surgical instruments will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
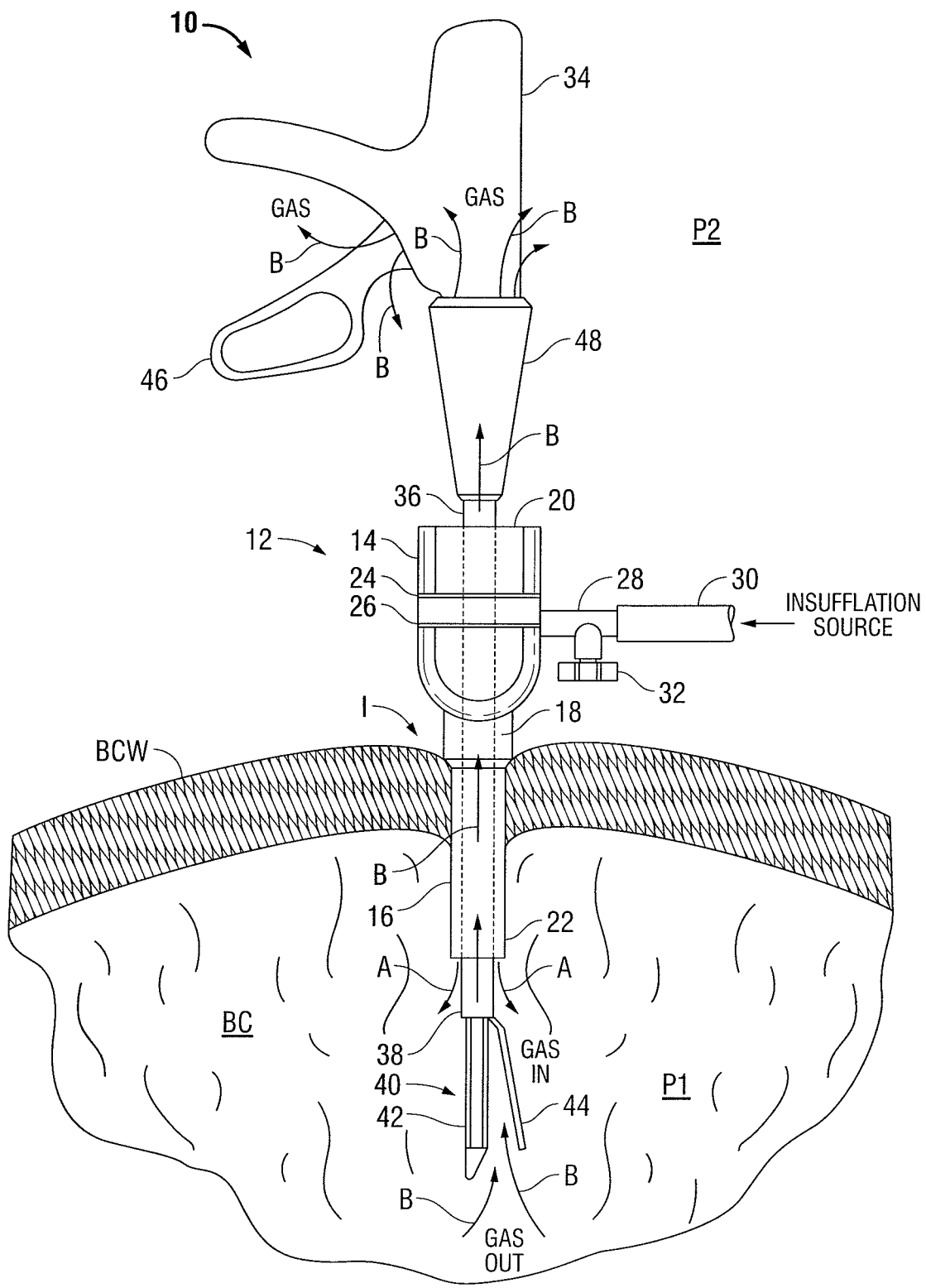
FIG. 1 is a side view, partially shown in section, of a prior art surgical instrument and prior art cannula inserted through a body cavity wall and into an insufflated or pressurized body cavity.

Referring initially to FIG. 1, there is illustrated a prior art surgical instrument 10 and a prior art cannula 12. Prior art cannula 12 is illustrated inserted through an incision I formed through a body cavity wall BCW and extending into a body cavity BC. Prior art cannula 12 is provided to receive a portion of prior art surgical instrument 10 therethrough so as to perform surgical operations within body cavity BC. Prior art cannula 12 generally includes a body portion 14 and a cannula tube 16 extending distally from body portion 14. Body portion 14 and cannula tube 16 form a throughbore 18 for receipt of portion of prior art surgical instrument 10. Throughbore 18 extends from a proximal end 20 of body portion 14 to an open distal end 22 of cannula tube 16.

A pair of seals, such as, for example, seals 24 and 26, may be provided within body portion 14 to prevent escape of gases out of body cavity BC and to seal about prior art surgical instrument 10. In order to pressurize and thereby create a working space within body cavity BC, a gas port 28 is provided on body portion 14 for receipt of a source of gas or insufflation fluid 30. Source of insufflation fluid 30 provides an inert, non-toxic gas such as, for example, carbon dioxide to expand and create a working space within body cavity BC. A valve 32 is provided on gas port 28 to control the flow of gas into body cavity BC.

Prior art surgical instrument 10 generally includes a handle or body portion 34 having an elongate tubular member 36 extending distally from body portion 34. An end effector 40 is located on a distal end 38 of elongate tubular member 36 in order to perform surgical operations on tissues located within body cavity BC. In prior art surgical instrument 10, end effector 40 includes a staple cartridge 42 and an anvil member 44 movably mounted relative to staple cartridge 42. Anvil member 44 is movable between an open position spaced from staple cartridge 42 to a closed position wherein anvil member 44 is in close cooperative alignment staple cartridge 42. While end effector 40 is illustrated as including staple cartridge 42 and anvil member 44, other types of end effectors such as, for example, cutters, graspers, biopsy devices, electrocautery devices, etc. are also contemplated for use in prior art surgical instrument 10. An actuator or trigger 46 is provided on body portion 34 and is operable to move anvil member 44 between the open and closed positions relative to staple cartridge 42. A rotator cuff 48 is rotatably mounted on body portion 34 and is affixed to elongate tubular member 36. Rotator cuff 48 is provided to rotate elongate tubular member 36, and thus end effector 40, in order to properly orient end effector 40 relative to the tissues being operated upon.

In using the prior art surgical instrument 10 and prior art cannula 12 to perform surgical operation within body cavity BC, incision I is formed through body cavity wall BCW and cannula tube 16 is inserted through incision I such that prior art cannula 12 forms an access port into body cavity BC. Once prior art cannula 12 is properly positioned, valve 32 is opened to allow insufflation gases to flow from source of insufflation fluid 30 through throughbore 18 and into body cavity BC in the direction of arrows A thereby expanding body cavity BC to create working space. As insufflation gases flow into body cavity BC, the pressure P1 within body cavity BC is raised to a level greater than an external or ambient pressure P2 outside of body cavity BC.

Once body cavity BC has been properly expanded and pressurized to pressure P1, prior art surgical instrument 10 is manipulated such that end effector 40 and elongate tubular member 36 are inserted through seals 24 and 26 and throughbore 18 in prior art cannula 12. Once end effector 40 has been extended out of distal end 22 of cannula tube 16, the desired surgical operation is performed within body cavity BC.

Because pressure P1 within body cavity BC is greater than pressure P2 outside of body cavity BC, there exists a pressure differential between end effector 40 located within body cavity BC and the remainder of prior art surgical instrument 10 such as, body portion 34, located outside of body cavity BC. Insufflation gases located within body cavity BC may, in some instances, be forced proximally through prior art surgical instrument 10 in the direction of arrows B and escape into body portion 34 and out between gaps between rotator cuff 48 and body portion 34 and trigger 46 and body portion 34. While prior art surgical instrument 10 typically includes various seals (not shown) to prevent escape of the insufflation gases, these seals may still leak, particularly as internal components of prior art surgical instrument 10 move relative to the seals during operation. As the insufflation gases move proximally through prior art surgical instrument 10, the insufflation gases tend to draw or siphon bodily fluids and tissue particles into and proximally through end effector 40 and elongate tubular member 36 thereby contaminating and in some instances potentially damaging internal components of prior art surgical instrument 10. Additionally, prior art surgical instrument 10 may provide a pathway for escape of the insufflation gases thereby lowering pressure P1 within body cavity BC.

Figure 2:
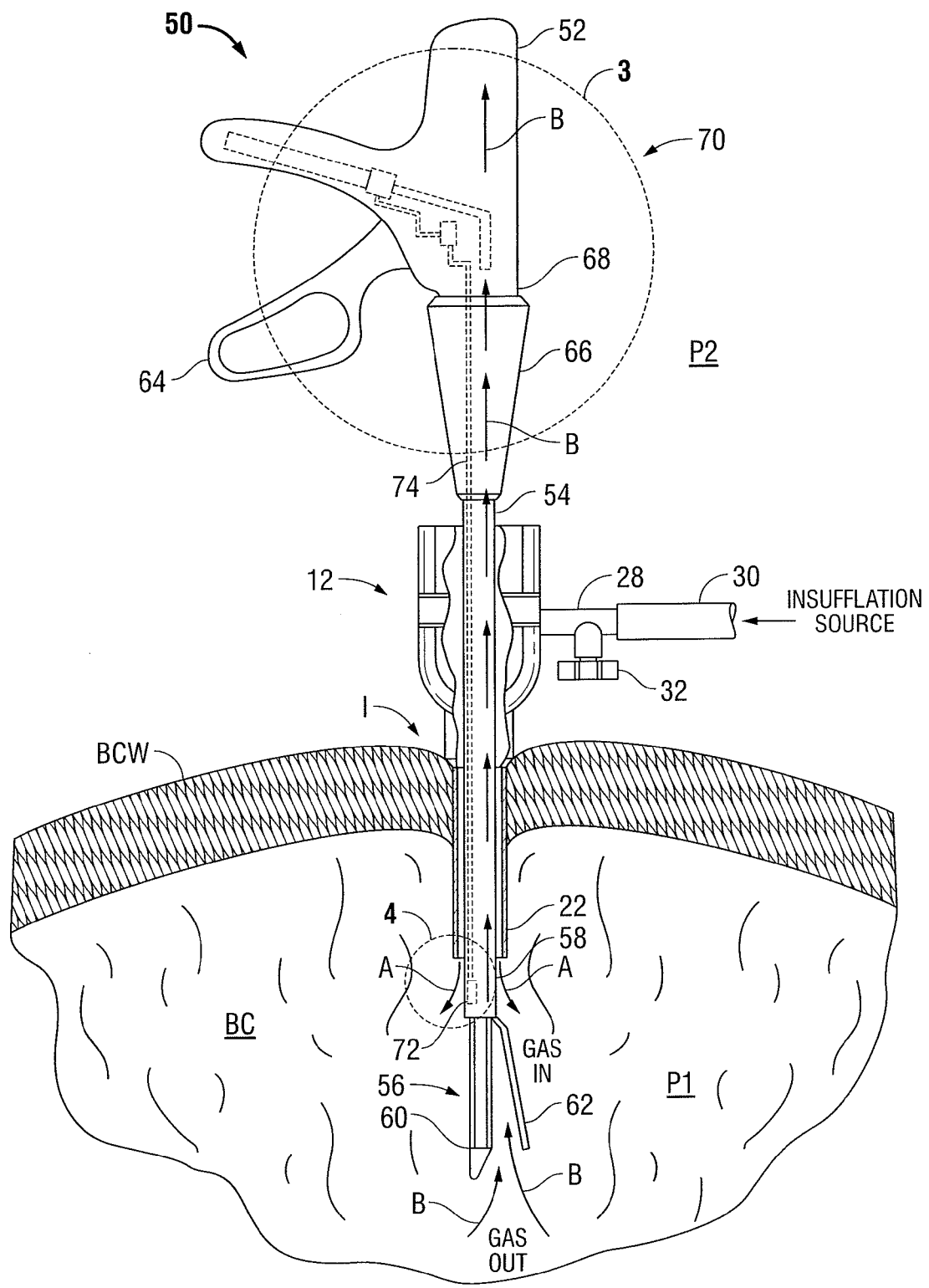
FIG. 2 is a side view, partially shown in section, of a first embodiment of a pressurized surgical instrument inserted through the prior art cannula and into the pressurized body cavity.

Referring now to FIG. 2, there is disclosed a pressurized surgical instrument 50 for use with prior art cannula 12 to perform a surgical operation within body cavity BC. Pressurized surgical instrument 50 is designed to inhibit the prevent escape of insufflation gases out of body cavity BC through pressurized surgical instrument 50. Pressurized surgical instrument 50 generally includes a handle or body portion 52 having an elongate tubular member 54 extending distally from body portion 52. An end effector 56 is mounted on a distal end 58 of elongate tubular member 54 and includes a staple cartridge 60 and an anvil member 62 movably mounted relative to staple cartridge 60. A trigger or actuator 64 is provided to move anvil member 62 from an open position spaced from staple cartridge 60 to a closed position adjacent staple cartridge 60. While pressurized surgical instrument 50 is disclosed as including end effector 56, other end effectors such as those noted hereinabove with respect to prior art surgical instrument 10 may be provided. A rotator cuff 66 is rotatably mounted on a distal end 68 of body portion 52 and is affixed to elongate tubular member 54 in order to properly orient end effector 56 relative to tissues being operated upon.

In order to prevent the escape of insufflation gases out of body cavity BC through pressurized surgical instrument 50, pressurized surgical instrument 50 includes a pressurization mechanism 70 which is provided to generate a pressure P3 (FIG. 5) within elongate tubular member 54 which is greater than or equal to pressure P1 within body cavity BC. The generation of pressure P3 within elongate tubular member 54 prevents the escape of insufflation gases and siphoning of bodily fluids and tissues into pressurized surgical instrument 50. A primary sensor 72 is located adjacent distal end 58 of elongate tubular member 54 and is provided to detect pressure P1. A sensor cable 74 extends through elongate tubular member 54 from primary sensor 72 to pressurization mechanism 70 in a manner described in more detail hereinbelow.

Referring now to FIG. 3, as noted hereinabove, actuator 64 is movably mounted relative to body portion 52. Actuator 64 is mounted to body portion 52 at pivot 76. In order to actuate end effector 56 (FIG. 2) a control rod 78 extends from an internal end 80 of actuator 64 and through elongate tubular member 54. A proximal end 82 of control rod 78 is movably affixed to internal end 80 by studs 84 formed on internal end 80. A distal end (not shown) of control rod 78 is affixed to end effector 56 to actuate end effector 56. As further noted hereinabove, surgical instruments typically include various seals to assist in preventing the escape of gases therethrough. Pressurized surgical instrument 50 includes a seal 86 located at a proximal end 88 of elongate tubular member 54 to seal about control rod 78.

Pressurization mechanism 70 includes an internal pressure monitoring and regulation circuit or controller 90 which is provided to receive a signal sent by primary sensor 72 and determine pressure P3 to be generated by pressurization mechanism 70. Controller 90 includes a comparison sensor 95 and a microprocessor or analog control circuit to compare pressure body cavity pressure P1 sensed by primary sensor 72 to ambient pressure P2 detected by the sensor 95 in controller 90 external of body cavity BC. Controller 90 triggers a valving or pressure regulation mechanism to generate and maintain internal surgical instrument pressure P3 at a level greater than or equal to pressure P1. A proximal end 92 of sensor cable 74 is connected to controller 90 to transmit the signal received from primary sensor 72.

Pressurization mechanism 70 additionally includes a self-contained gas canister 94 positioned within body portion 52. Self-contained gas canister 94 contains a carbon dioxide insufflation gas. A valve 96 is provided on self-contained gas canister 94 to regulate the flow of gas out of self-contained gas canister 94 and through pressurized surgical instrument 50. A valve cable 98 extends from controller 90 to valve 96. Controller 90 compares pressure P1 detected by primary sensor 72 and triggers valve 96 to open in order to provide gas pressure P3 within pressurized surgical instrument 50. Self-contained gas canister 94, valve 96 and valve cable 98 form a pressure delivery system 100 of pressurization mechanism 70.

Pressure delivery system 100 additionally includes a pressure tube 102 having a first end 104 connected to valve 96 and a second end 106 which is connected to a proximal end of 108 of elongate tubular member 54 distally of seal 86. Specifically, a collar 110 is in fluid communication with elongate tubular member 54 through a plurality of ports 112 formed in collar 110. Second end 106 of pressure tube 102 is affixed to collar 110 to transmit pressurization gases or insufflation fluids from self-contained gas canister 94 to elongate tubular member 54.

Referring for the moment to FIG. 4A, as noted hereinabove, primary sensor 72 is located adjacent distal end 58 of elongate tubular member 54. A distal end 114 of sensor cable 74 is affixed to primary sensor 72. Primary sensor 72 may be affixed to an inner surface 116 of elongate tubular member 54 or, alternatively, primary sensor 72 may be formed, molded, or otherwise positioned internally of a wall 118 of elongate tubular member 54. Additionally, sensor cable 74 may also extend internally of wall 118 from primary sensor 72 proximally to proximal end 88 of elongate tubular member 54, as shown in FIG. 4B. It should be noted that, while primary sensor 72 is disclosed as being located within elongate tubular member 54, primary sensor 72 can be located elsewhere within pressurized surgical instrument 50.

Referring now to FIGS. 2-6, and initially with regard to FIG. 2, the use of pressurized surgical instrument 50 will now be described. Prior art cannula 12 is inserted through incision I formed through body cavity wall BCW such that distal end 22 of prior art cannula 12 is located within body cavity BC. Thereafter, valve 32 is opened to allow gases to flow from source of insufflation fluid 30 through gas port 28 and out distal end 22 of prior art cannula 12. The gas flows in the direction of arrows A to insufflate body cavity BC to pressure P1 which is greater than ambient pressure P2 and to create a working space within body cavity BC. Similar to prior art surgical instrument 10 described hereinabove, when pressurized surgical instrument 50 is in a static or non-actuated condition, insufflation gases can flow proximally through pressurized surgical instrument 50 in the direction of arrows B thereby siphoning insufflation fluids and body tissues into and through pressurized surgical instrument 50.

Figure 5:
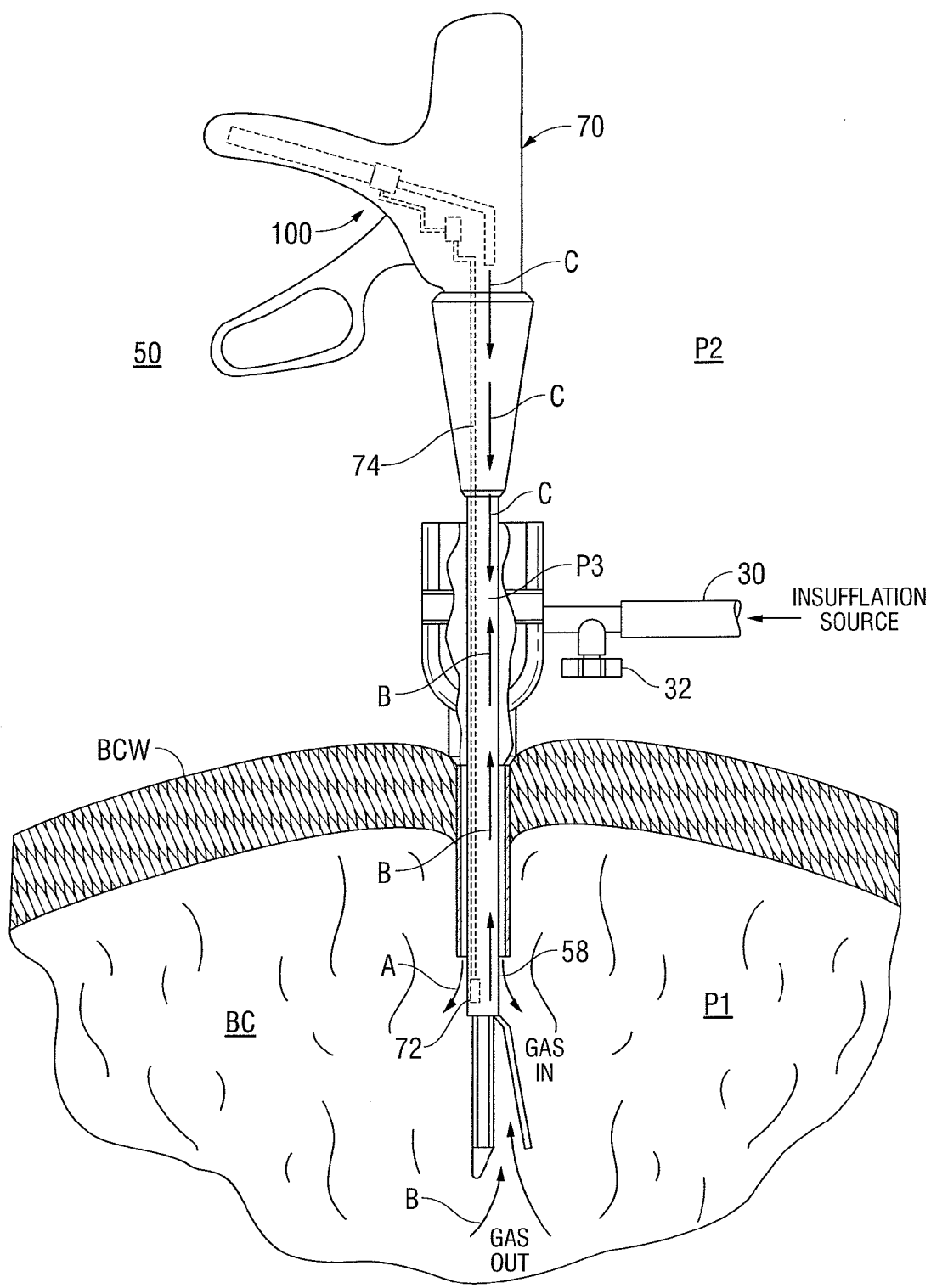
FIG. 5 is a view similar to FIG. 2 illustrating actuation of the self-contained pressurization mechanism to equalize pressure within the elongate tubular member.

Referring now to FIGS. 3 and 5, upon actuation of pressurization mechanism 70, controller 90 (FIG. 3) receives a signal proportional to pressure P1 detected by primary sensor 72 and compares it to pressure P3 within pressurized surgical instrument 50. Should pressure P1 be greater than P3, controller 90 signals pressure delivery system 100, including valve 96, to open allowing high pressure gases to flow from self-contained gas canister 94 through pressure tube 102 to collar 110 at proximal end 108 of elongate tubular member 54. This initiates the flow of gases distally in the direction of arrows C through pressurized surgical instrument 50. As gases flow distally in the direction of arrows C through pressurized surgical instrument 50, the pressure within pressurized surgical instrument 50 is equalized such that pressure P3 within pressurized surgical instrument 50 is equal to pressure P1 within body cavity BC thereby preventing any flow or siphoning of bodily fluids or tissues proximally through pressurized surgical instrument 50. It should be noted that controller 90 can be adjusted to provide a pressure P3 which is equal to pressure P1 or greater than pressure P1.

Figure 6:
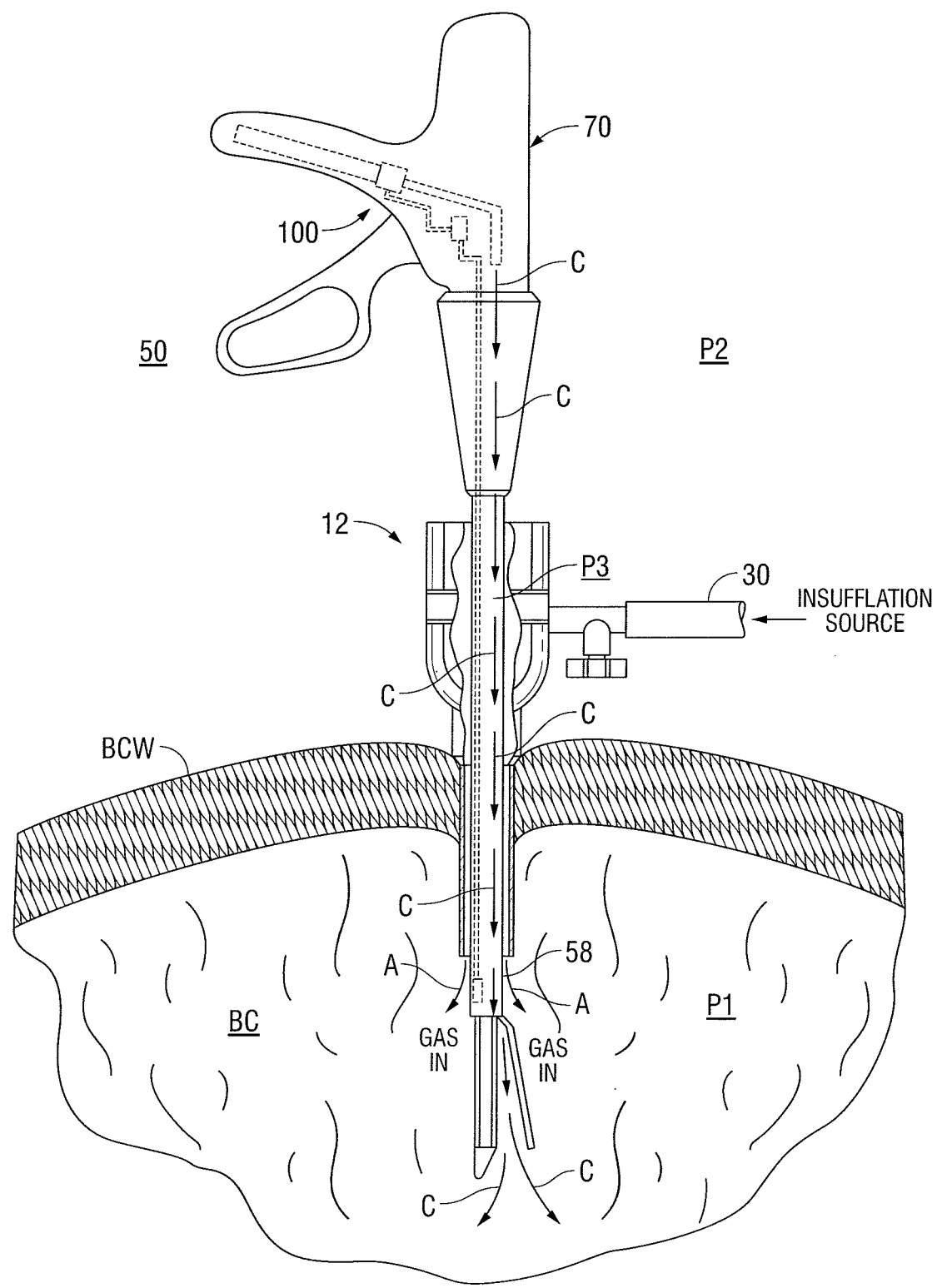
FIG. 6 is a view similar to FIG. 2 illustrating the actuation of the self-contained pressurization mechanism to create a pressure within the surgical instrument which is greater than the pressure within the pressurized body cavity.

Referring now to FIG. 6, and as noted hereinabove, controller 90 can be adjusted to provide a pressure P3 which is greater than pressure P1 within body cavity BC. This is desirable where additional insufflation fluid may be necessary to maintain body cavity BC in the insufflated condition and prevent against loss of insufflation gases through additional access ports or prior art cannulas 12. In this instance, controller 90 triggers pressure delivery system 100 to provide a flow of high pressure gases, having a pressure P3 greater than P1, in the direction of arrows C through pressurized surgical instrument 50 and out distal end 58 of elongate tubular member 54 and into body cavity BC.

In this manner, pressurized surgical instrument 50 prevents siphoning of bodily fluids and tissues back through pressurized surgical instrument 50 and can be utilized to provide additional insufflation fluids within body cavity BC to offset any losses through other access ports.

Figure 7:
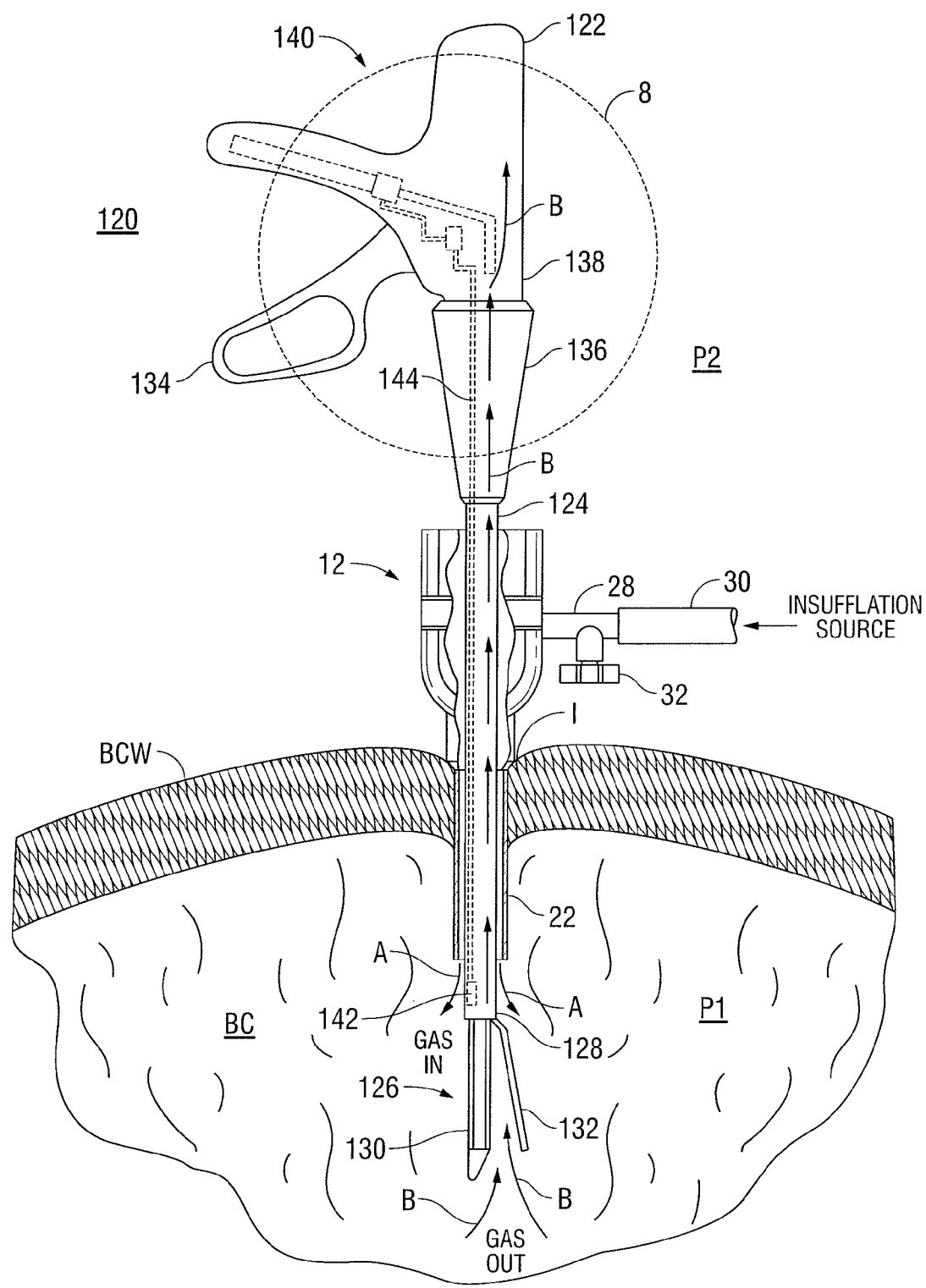
FIG. 7 is a side view, partially shown in section, of an alternative embodiment of a pressurized surgical instrument inserted through the prior art cannula and into the pressurized body cavity.

Referring now to FIGS. 7-10, and initially with respect to FIG. 7, there is disclosed another alternative embodiment of a pressurized surgical instrument 120 for use with prior art cannula 12 to perform a surgical operation within body cavity BC. Like pressurized surgical instrument 50 described hereinabove, pressurized surgical instrument 120 is designed to prevent escape of insufflation gases out of the cavity BC and thus prevent siphoning of any bodily fluids or tissues through pressurized surgical instrument 120. The operational structure of pressurized surgical instrument 120 is similar to that of pressurized surgical instrument 50 and generally includes a handle or body portion 122 having an elongate tubular member 124 extending distally from body portion 122. An end effector 126 is mounted on a distal end 128 of elongate tubular member 124 and includes a staple cartridge 130 and an anvil member 132. Anvil member 132 was movably mounted relative to staple cartridge 130. A trigger or actuator 134 is provided to move anvil member 62 from an open position spaced from staple cartridge 130 to a closed position adjacent staple cartridge 130. A rotator cuff 136 is rotatably mounted on a distal end 138 of body portion 132 to orient end effector 126 relative to tissue being operated upon.

Pressurized surgical instrument 120 includes a pressurization mechanism 140 to prevent the escape of insufflation gases out of body cavity BC through pressurized surgical instrument 120. Pressurization mechanism 140 is provided to generate a pressure P4 (FIG. 9) within elongate tubular member 124 which is greater than or equal to pressure P1 within body cavity BC. A primary sensor 142 is located adjacent distal end 128 of elongate tubular member 124 and is provided to detect pressure P1 in the manner described hereinabove. A sensor cable 144 extends through elongate tubular member 124 from primary sensor 142 to pressurization mechanism 140. Similar to primary sensor 72 and sensor cable 74 in pressurized surgical instrument 50, primary sensor 142 and sensor cable 144 may be provided on an inside of elongate tubular 124 or may be contained within a wall of elongate tubular member 124.

Figure 8:
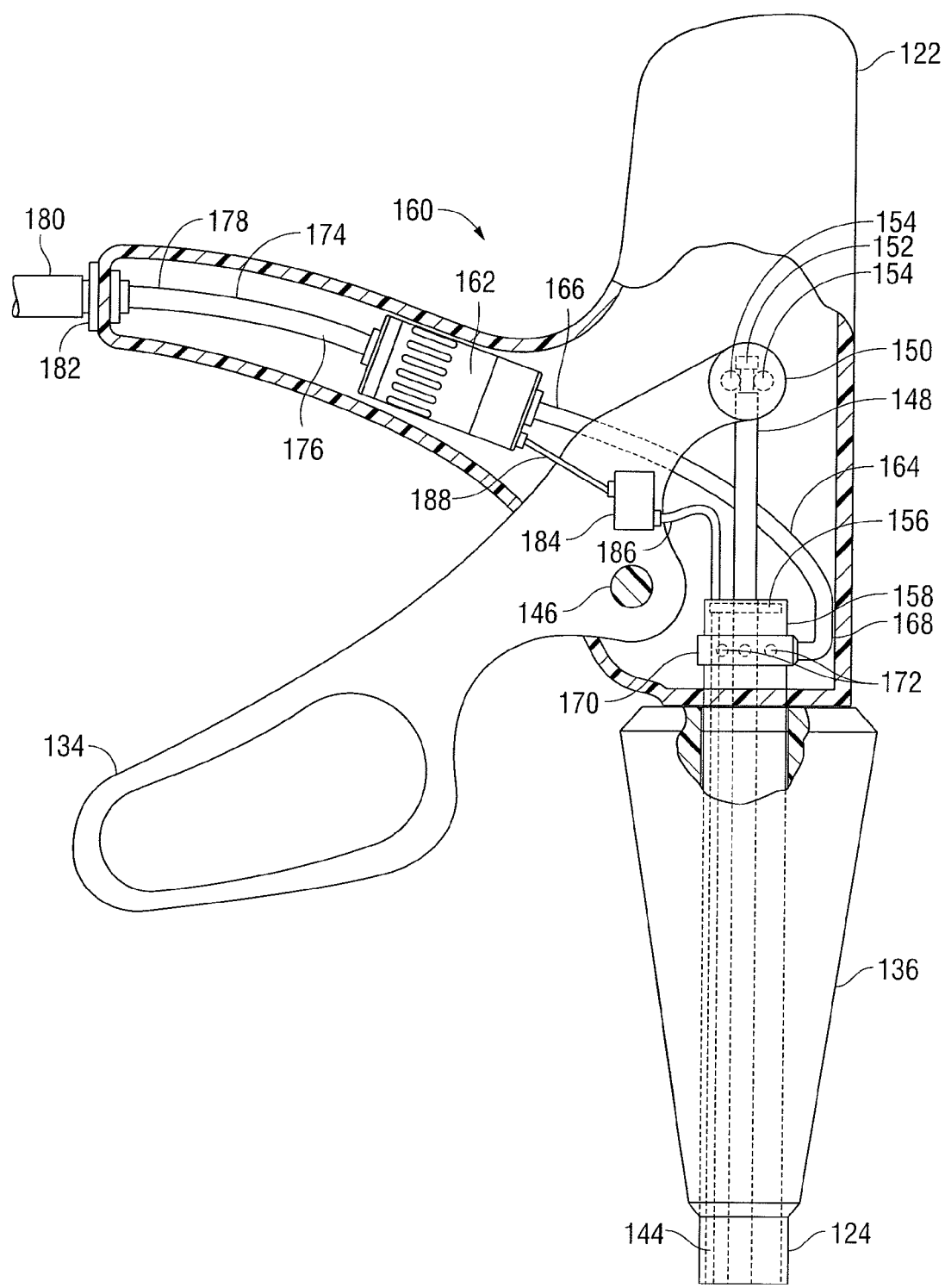
FIG. 8 is an enlarged area of detail view of FIG. 7 illustrating an alternative embodiment of a pressurization mechanism located within a handle or body portion of the pressurized surgical instrument.

Referring now to FIG. 8, actuator 134 is movably mounted relative to body portion 122 at a pivot 146. A control rod 148 extends from an internal end 150 of actuator 134 through elongate tubular member 124 to end effector 126. Translation of control rod 148 through elongate tubular member 124 by actuation of actuator 134 moves anvil member 132 between the open and closed positions relative to staple cartridge 130 in a known manner. A proximal end 152 of control rod 148 is secured to internal end 150 of actuator 134 by studs 154. A seal 156 is provided within a proximal end 158 of elongate tubular member 124 to minimize escape of insufflation gases out of body cavity BC through elongate tubular member 124.

Pressurizing mechanism 140 additionally includes a pressure delivery system 160 incorporating a pressurizing pump 162. Pressurizing pump 162 is provided to generate pressure P4 which is greater than or equal to pressure P1 located within body cavity BC. Pressure delivery system 160 additionally includes a pressure tube 164 having a proximal end 166 connected to pressurizing pump 162 and a distal end 168 which is connected to a collar 170 provided on proximal end 158 of elongate tubular member 124. Collar 170 is located distally of seal 156 and includes a plurality of ports 172 which are in fluid communication within an interior of elongate tubular member 124.

Pressurizing pump 162 can be powered by a variety of means such as, for example, internal batteries, external power sources, etc. Additionally, pressurizing pump 162 can draw its pressurizing fluid from external air sources in the instance where pressure P4 is to be equal to pressure P1 or maybe connected to an external source of low pressure insufflation fluids when it is desired to generate pressure P4 greater than pressure P1. Pressure delivery system 160 additionally includes a draw tube 174 having a first end 176 connected to pressurizing pump 162 and a second end 178 connected to an external source of insufflation fluids. An external tube 180 is provided for connection to the external source of insufflation fluids and is connected to second end 178. A bushing 182 may be provided to connect second end 178 of draw tube 174 to external tube 180.

Pressurization mechanism 140 additionally includes a controller 184 which functions substantially identical to controller 90 described hereinabove with respect to pressurized surgical instrument 50. A proximal end 186 of sensor cable 144 is connected to controller 184 to transmit a signal detected by primary sensor 142. A pump cable 188 extends between controller 184 and pressurizing pump 162. Controller 184 receives a signal from primary sensor 142 and sends an instructional signal to pressurizing pump 162 in order to generate the desired pressure P4.

Referring now to FIGS. 7 through 10, the use of pressurizing mechanism 140 to generate pressures within pressurized surgical instrument 120 will now be described. Cannula 12 is positioned through body cavity wall BCW in the manner described hereinabove and body cavity BC is insufflated to a pressure P1 to create a working space. Thereafter, pressurized surgical instrument 120 is manipulated through cannula 12 such that end effector 126 is positioned within body cavity BC.

Referring initially to FIG. 7, in the initial or nonactivated state, insufflation gases are forced into body cavity BC through prior art cannula 12 in the direction of arrows A. When pressurizing mechanism 140 is not activated pressure P1 within body cavity BC is greater than pressure P2 outside body cavity BC thereby allowing insufflation gases to flow in the direction of arrows B through pressurized surgical instrument 120. As noted hereinabove, the escape of insufflation gases in the direction of arrows B causes a drawing or siphoning effect bowling bodily fluids and tissues into pressurized surgical instrument 120.

Figure 9:
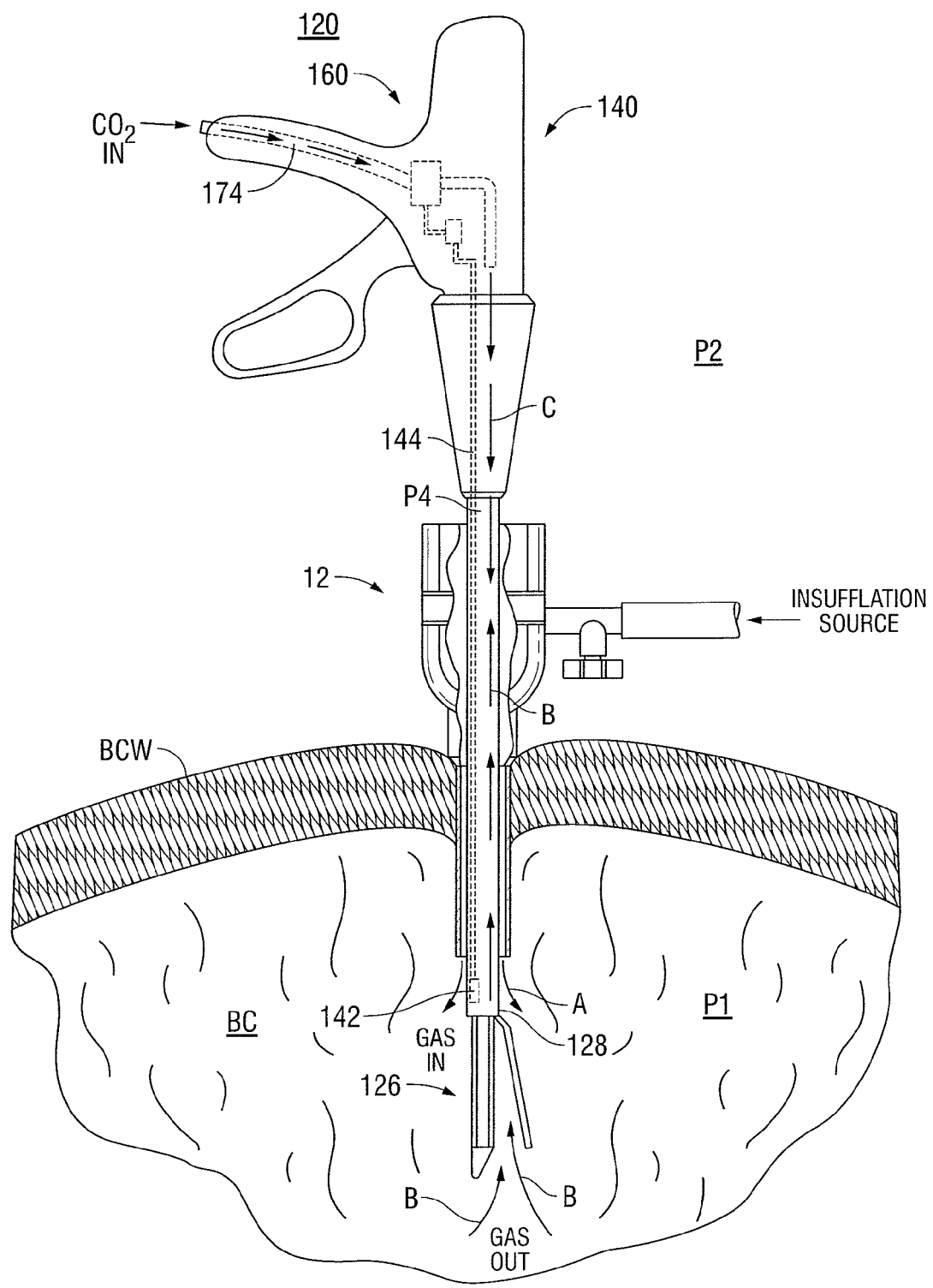
FIG. 9 is a view similar to FIG. 7 illustrating the actuation of the pressurization mechanism to equalize pressure within an elongate tubular member of the pressurized surgical instrument.

Referring now to FIGS. 8 and 9, when it is desired to prevent siphoning of bodily fluids through pressurized surgical instrument 120, pressurized surgical instrument 120 is activated such that primary sensor 142 detects pressure P1 within body cavity BC. The signal detected by primary sensor 142 is sent to pressurization mechanism 140 through sensor cable 144. Specifically, the signal is sent to controller 184 of pressurization mechanism 140 which then sends a signal to pressure delivery system 160. Pressurizing pump 162 is activated and draws fluid through draw tube 174 and forces the fluid through pressure tube 164 into elongate tubular member 124. Fluid pressure is driven along lines of arrows C to generate pressure P4 within elongate tubular member 124 of pressurized surgical instrument 120. As shown, generated pressure P4 is equal to body cavity pressure P1 which equalizes pressures within pressurized surgical instrument 120 to prevent any siphoning or escape of bodily fluids or tissues.

Figure 10:
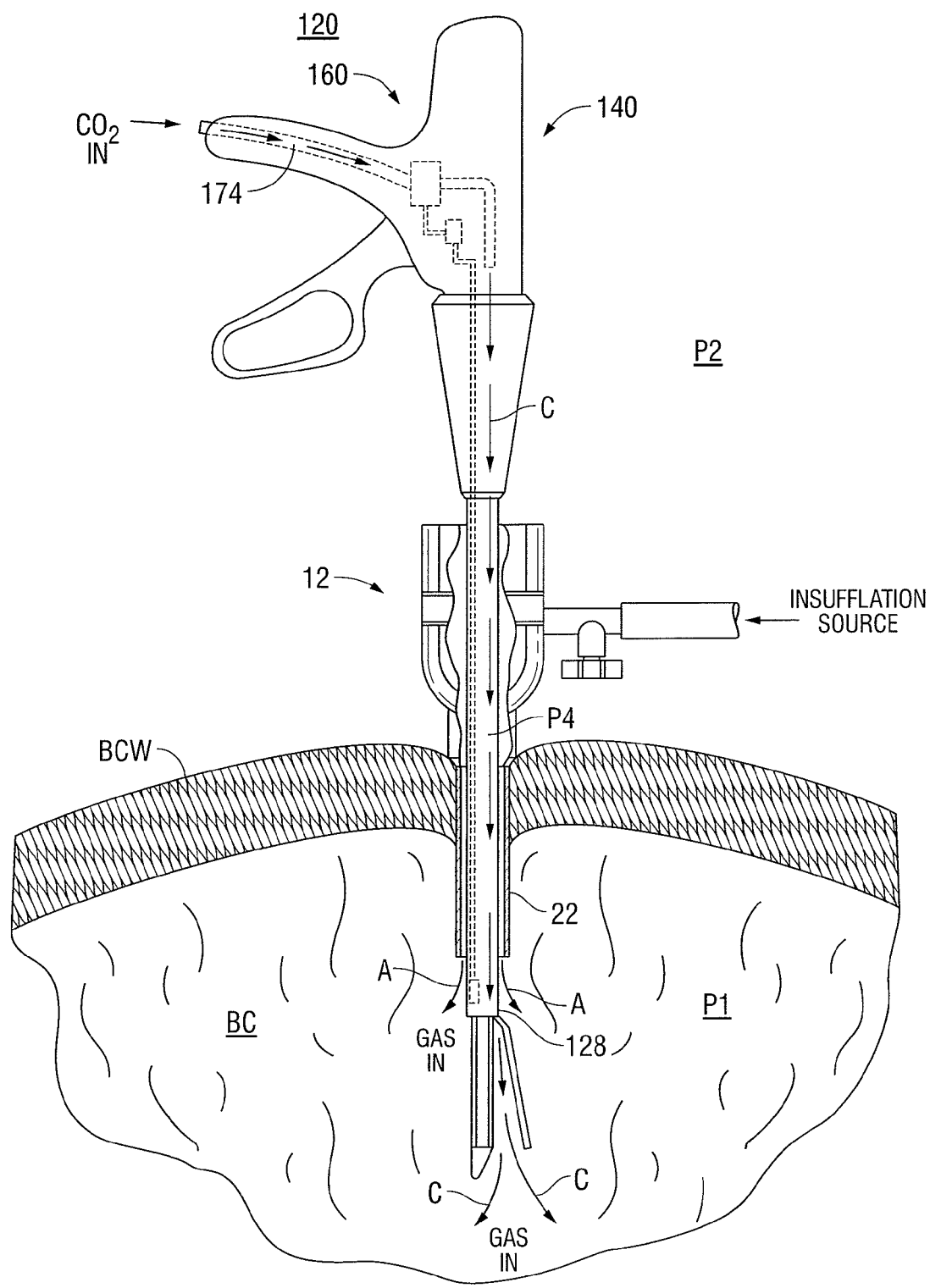
FIG. 10 is a view similar to FIG. 7 illustrating the actuation of the pressurization mechanism to create a pressure within the surgical instrument which is greater than the pressure within the pressurized body cavity.

Referring now to FIG. 10, in the event it is desirable to provide additional insufflation fluid into body cavity BC, the signal sent from controller 184 to pressurizing pump 162 is such that pressurizing pump 162 generates a pressure P4 greater than body cavity pressure P1. As shown, pressurizing gases generated by pressurizing pump 162 travel through pressurized surgical instrument 120 in the direction of arrows C and exit distal end 128 of elongate tubular member 124 and into body cavity BC.

In this manner, pressurized surgical instrument 120 incorporates an internal pressurizing pump 162 within pressure delivery system 160 of pressurizing mechanism 140 to either balance the pressures within pressurized surgical instrument 120 or generate sufficient pressure to provide additional sources of insufflation fluid into body cavity BC.

Referring now to FIGS. 11 through 14, there is disclosed another embodiment of a pressurized surgical instrument 190. Pressurized surgical instrument 190 generally includes a handle or body portion 192 and an elongate tubular member 194 extending distally from body portion 192. An end effector 196 is provided on a distal end 198 of elongate tubular member 194. End effector 196 includes a staple cartridge 200 and an anvil member 202 movably mounted to staple cartridge 200. A trigger or actuator 204 is movably mounted on body portion 192 and is provided to move anvil member 202 from an open position spaced from staple cartridge 200 to a closed position adjacent staple cartridge 200. A rotator cuff 206 is rotatably mounted on a distal end 208 of body portion 192 and is rotatable to orient end effector 196 relative to tissues being operated upon.

Pressurized surgical instrument 190 includes a pressurization mechanism 210 to prevent the escape of insufflation gases and siphoning of bodily fluids through pressurized surgical instrument 190. A primary sensor 212 is positioned adjacent distal end 198 of elongate tubular member 194 and a sensor cable 214 extends between primary sensor 212 and pressurization mechanism 210. It should be noted that, similar to the above embodiments, primary sensor 212 and sensor cable 214 may be contained within a wall (not shown) of elongate tubular member 194.

In contrast to the previously disclosed embodiments, pressurized surgical instrument 190 utilizes an external source 216 of high pressure insufflation gases. A supply tube 218 is provided and extends from external source 216 and is connected to a pressure delivery system 220 provided within body portion 192 in the manner described in more detail hereinbelow.

Figure 12:
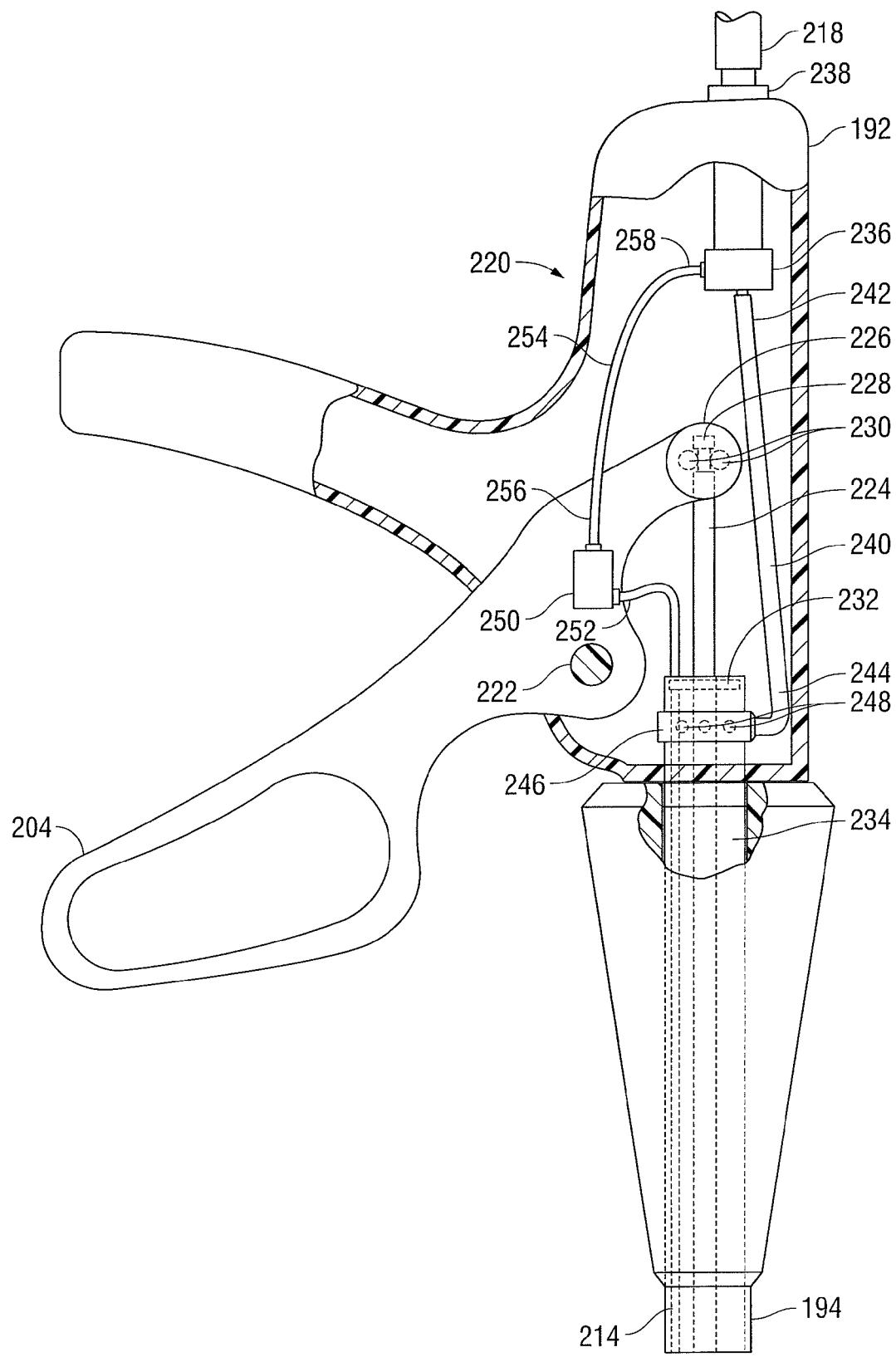
FIG. 12 is an enlarged area of detail view of FIG. 11 illustrating a further alternative embodiment of a pressurization mechanism located within a handle or body portion of the pressurized surgical instrument.

Referring to FIG. 12, actuator 204 is movably mounted to body portion 192 at a pivot 222. A control rod 224 extends through elongate tubular member 194 and is connected to an internal end 226 of actuator 204 at its proximal end 228. Studs 230 formed on internal end 226 secure proximal end 228 of control rod 224 to actuator 204. A seal 232 is provided in a proximal end 234 of elongate tubular member 194 to assist in the prevention of escape of insufflation gases.

In this embodiment, pressure delivery system 220 generally includes a valve 236 incorporating a fitting 238 for releasable attachment to supply tube 218. A pressure tube 240 is provided and extends between valve 236 and elongate tubular member 234. Specifically a proximal end 242 of pressure tube 240 is connected to valve 236 and a distal end 244 of pressure tube 240 is connected to a collar 246 provided about proximal end 234 of elongate tubular member 194. Collar 246 is in fluid communication with elongate tubular member 194 through a series of ports 248.

Pressurization mechanism 210 includes a controller 250 which is substantially similar to those controllers described hereinabove with regard to pressurized surgical instruments 50 and 120. A proximal end 252 of sensor cable 214 is connected to controller 250 to transmit a signal comparable to the pressure detected by primary sensor 212. A valve cable 254 is provided and has a first end 256 connected to controller 250 and a second end 258 connected to valve 236. Controller 250 receives signals sent through sensor cable 214 and transmits a signal along valve cable 254 to control the operation of valve 236.

Figure 11:
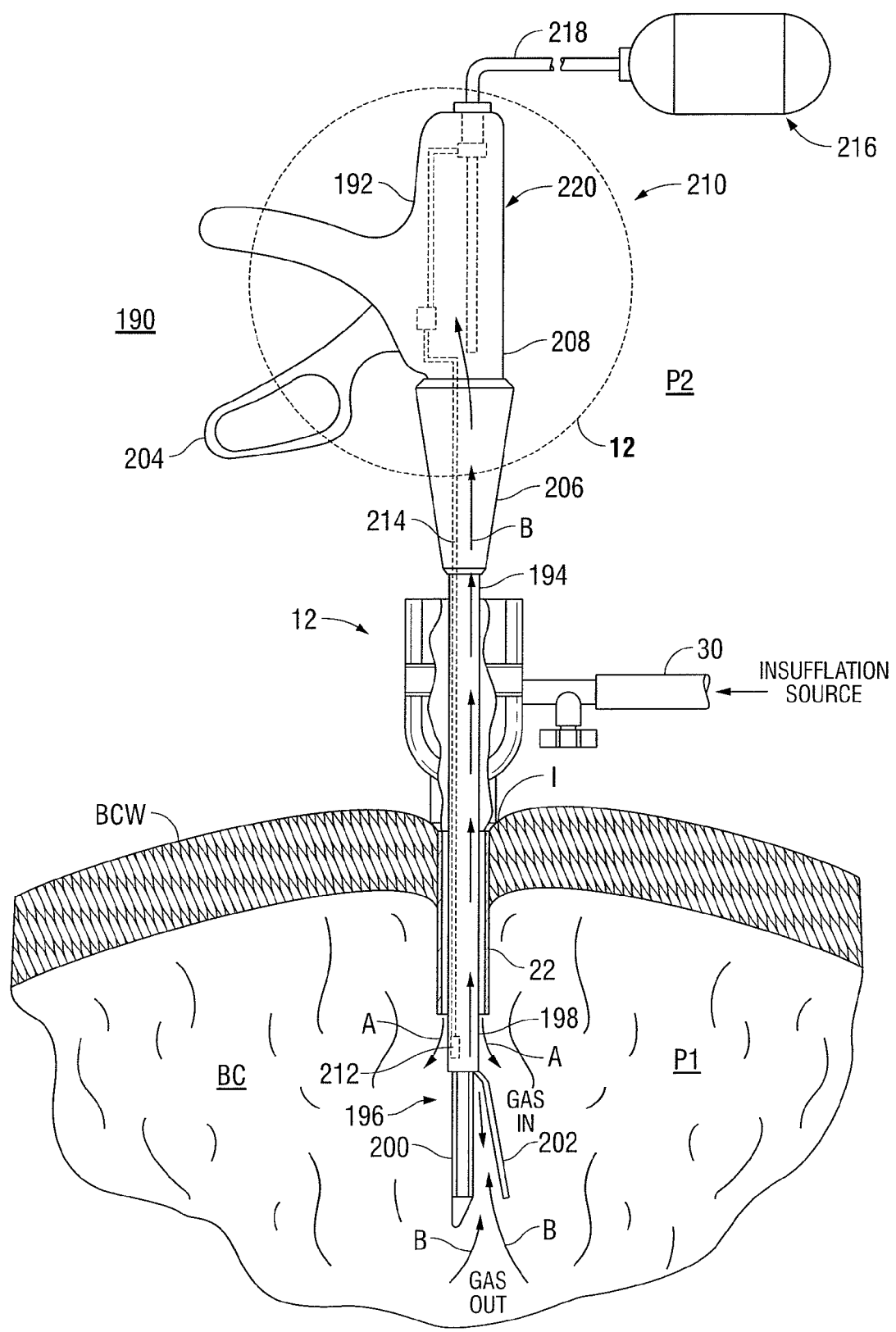
FIG. 11 is a side view, partially shown in section, of a further alternative embodiment of a pressurized surgical instrument inserted through the prior art cannula and into a pressurized body cavity.

Referring now to FIGS. 11-14, and initially with regard to FIG. 11, the operation of pressurized surgical instrument 190 will now be described. Cannula 12 is inserted through an incision I formed through body cavity wall BCW and body cavity BC is insufflated to a pressure P1 to create a working space within body cavity BC. Thereafter, pressurized surgical instrument 190 is manipulated through cannula 12 to position end effector 196 within body cavity BC. As with prior examples, prior to activation of pressurization mechanism 210, insufflation fluids may flow-through pressurized surgical instrument 190 in the direction of arrows B thereby creating a siphoning effect drawing bodily fluids and tissue into pressurized surgical instrument 190.

Figure 13:
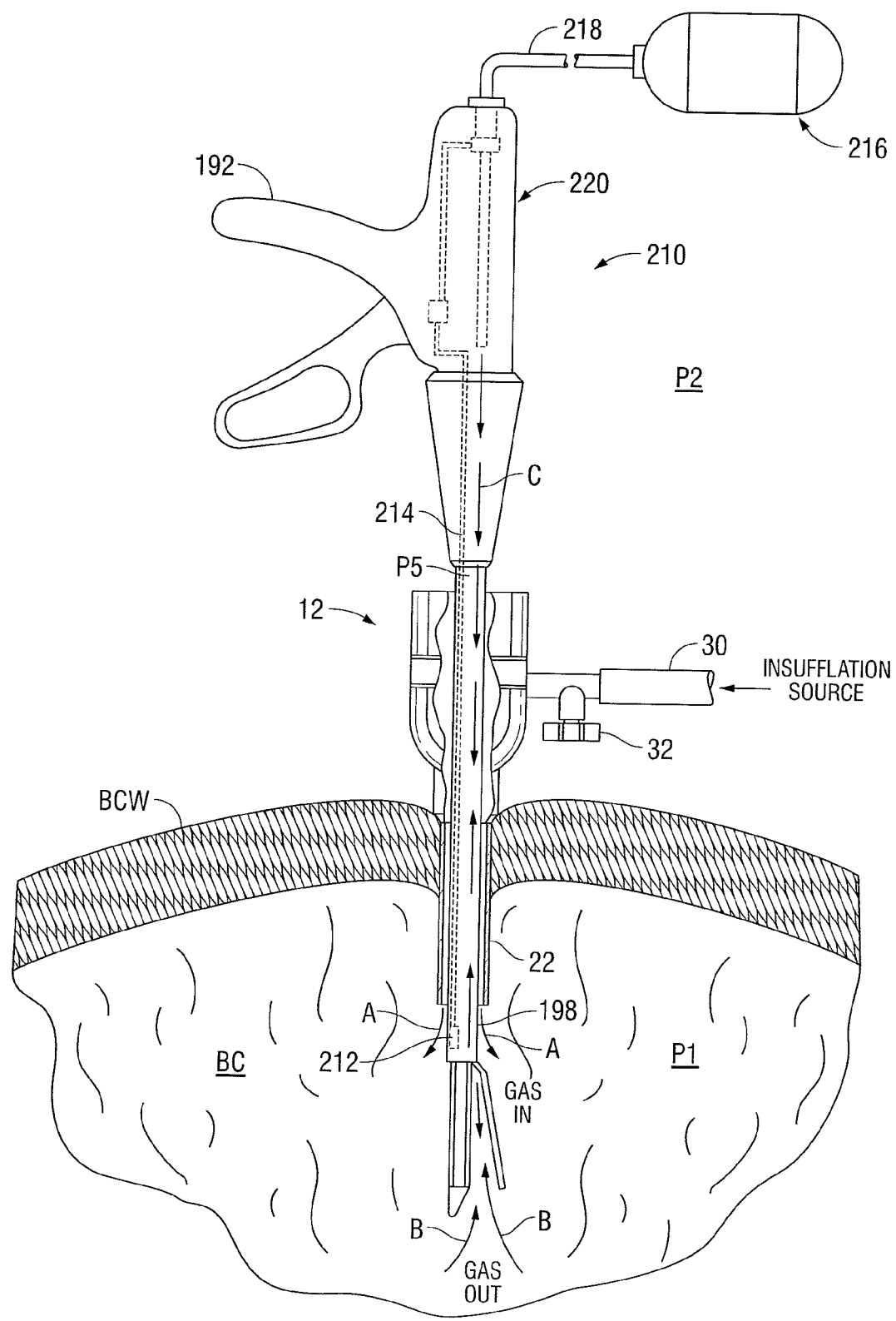
FIG. 13 is a view similar to FIG. 11 illustrating the actuation of the pressurization mechanism to equalize pressure within an elongate tubular member of the pressurized surgical instruments.

Referring now to FIGS. 12 and 13, upon activation of pressurization mechanism 210, primary sensor 212 detects pressure P1 and sends a signal along sensor cable 214 to controller 250. Controller 250 then sends a signal via valve cable 254 to valve 236. Depending upon the desired state of pressurized surgical instrument 190, valve 236 is opened to receive external source 216 of high pressure insufflation fluid via supply tube 218 and allow the insufflation fluids to flow-through pressure tube 240 to collar 246. Valve 236 is opened to a degree which allows a pressure P5, equal to pressure P1 within body cavity BC, to pass through and into pressure tube 240. The high pressure insufflation fluids flow through ports 248 and into elongate tubular member 194. The insufflation fluids flow distally in the direction of arrows C to equalize pressure within pressurized surgical instrument 190.

Figure 14:
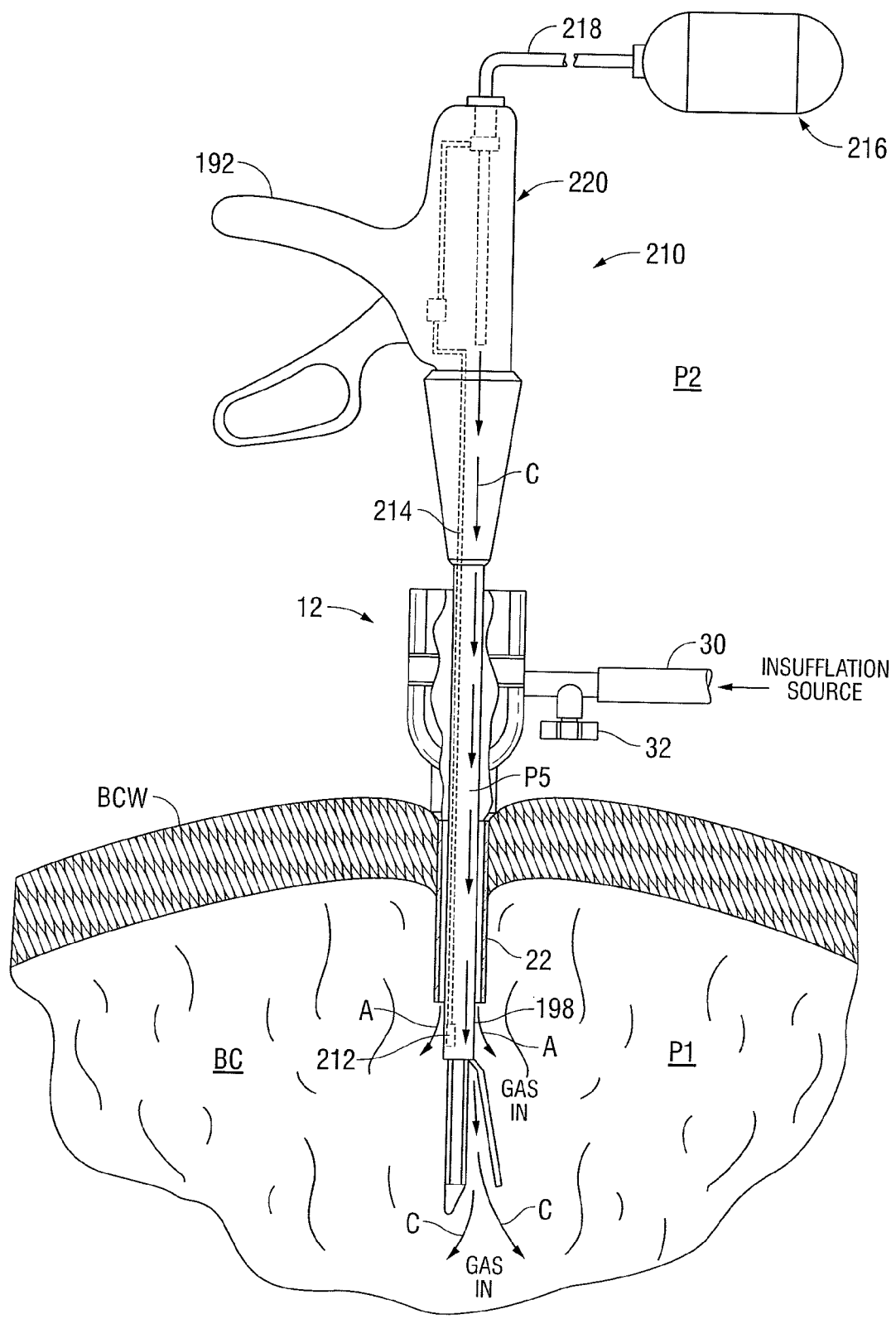
FIG. 14 is a view similar to FIG. 11 illustrating the actuation of the pressurization mechanism to create a pressure within the pressurized surgical instrument which is greater than the pressure within the pressurized body cavity.

Referring to FIG. 14, in the event it is desired to utilize external source 216 of insufflation fluids to provide additional insufflation fluid into body cavity BC, valve 236 is opened to a degree which allows pressure P5 to be greater than pressure P1 located within body cavity BC. In this instance, insufflation fluids flow in the direction of arrows C completely through pressurized surgical instrument 190 and into body cavity BC.

In this manner, pressurized surgical instrument 190 can be equalized to pressure P1 contained within body cavity BC or can be pressurized to a degree higher than pressure P1 in body cavity BC and utilized to provide an additional source of insufflation gases. Additionally, by utilizing an external source 216 of pressurized insufflation fluids, pressurized surgical instrument 190 can receive and essentially unlimited supply of pressurization gases.

As discussed above, pressurized surgical instruments 50, 120 and 190 incorporate provisions to equalize pressures within the respective surgical instruments relative to pressures inside an insufflated body cavity BC, as well as, provide an additional source of insufflation fluids into body cavity BC to offset losses through other access ports.

It will be understood that various modifications may be made to the embodiments disclosed herein. For example, the disclosed pressurization mechanisms, primary sensors and sensor cables may be incorporated into other instruments utilized in endoscopic and/or laparoscopic procedures such as, for example, endoscopic biopsy devices, visualization devices, etc. Further, and as noted hereinabove, the primary sensor may be located at various locations within the surgical instrument so as to detect pressures within the surgical instrument at various points. Additionally, seals may be provided at the openings in the surgical instruments body portions which receive the actuators, rotator cuff and any other external devices and the entire surgical instrument including the body portion, as well as the elongate tubular member portion, may be pressurized. Therefore, the above description should not be construed as limiting, but merely as exemplifications of particular embodiments. Those skilled in the art will envision other modifications within the scope and spirit of the claims appended hereto.

The invention claimed is:

1. A pressurized surgical instrument comprising:
 a surgical instrument having a body portion and an elongate tubular member extending from the body portion, the elongate tubular member defining an interior;
 a primary sensor positioned within the surgical instrument for detecting a pressure in a working environment, the working environment surrounding the elongate tubular member; and
 a pressurization mechanism positioned within the body portion of the surgical instrument, the pressurization mechanism including a controller connected to the primary sensor and a pressure delivery system connected to the controller, the pressure delivery system being in fluid communication with an interior of the surgical instrument and configured to provide an insufflation fluid in response to a pressure detected by the primary sensor and to maintain a desired pressure within the interior of the elongate tubular member.

2. The pressurized surgical instrument as recited in claim 1, wherein the controller incorporates a second sensor for detecting a pressure within the surgical instrument, the controller comparing the pressure in the working environment with the pressure within the surgical instrument.

3. The pressurized surgical instrument as recited in claim 1, wherein the pressure delivery system is in fluid communication with the interior of the elongate tubular member through a tube.

4. The pressurized surgical instrument as recited in claim 3, wherein a distal end of the tube is connected to a collar in fluid communication with a proximal end of the elongate tubular member.

5. The pressurized surgical instrument as recited in claim 4, wherein the collar is in fluid communication with the proximal end of the elongate tubular member through a series of ports positioned about the collar.

6. The pressurized surgical instrument as recited in claim 1, wherein the pressure delivery system includes a self-contained gas cartridge positioned within the body portion of the surgical instrument.

7. The pressurized surgical instrument as recited in claim 6, wherein the pressure delivery system includes a valve connected to the self-contained gas cartridge and to the controller, such that the valve regulates gas released by the self-contained gas cartridge in response to a signal received from the controller.

8. The pressurized surgical instrument as recited in claim 1, wherein the pressure delivery system includes a pressurizing pump in fluid communication with the interior of the elongate tubular member and connected to the controller.

9. The pressurized surgical instrument as recited in claim 8, wherein the pressure delivery system additionally includes a draw tube extending from the pressurized pump to a location external of the body portion.

10. The pressurized surgical instrument as recited in claim 8, wherein the pressurizing pump transmits gas in response to a signal received from the controller.

11. The pressurized surgical instrument as recited in claim 1, wherein the pressure delivery system includes a valve and a connection tube extending from the valve to a connection fitting, the valve connected to the controller.

12. The pressurized surgical instrument as recited in claim 11, wherein the connection fitting is releasably attachable to an external source of insufflation fluid.

13. The pressurized surgical instrument as recited in claim 11, wherein the valve regulates gas released by a pressurized pump in response to a signal received from the controller.

14. The pressurized surgical instrument as recited in claim 1, wherein the primary sensor is positioned within the elongate tubular member.

15. The pressurized surgical instrument as recited in claim 14, wherein the primary sensor is positioned adjacent a distal end of the elongate tubular member.

16. The pressurized surgical instrument as recited in claim 14, wherein the primary sensor is contained within a wall of the elongate tubular member.

17. The pressurized surgical instrument as recited in claim 1, wherein the primary sensor is connected to the controller through a sensor cable.

18. The pressurized surgical instrument as recited in claim 17, wherein the sensor cable is contained within a wall of the elongate tubular member.

19. The pressurized surgical instrument as recited in claim 1, wherein the elongate tubular member incorporates a seal to prevent loss of insufflation fluid.

20. The pressurized surgical instrument as recited in claim 1, wherein the surgical instrument further includes an end effector extending from the elongate tubular member.

21. The pressurized surgical instrument as recited in claim 20, wherein the end effector includes an anvil member moveable relative to a staple cartridge.

22. The pressurized surgical instrument recited in claim 1, wherein the primary sensor is positioned adjacent a distal end of the elongate tubular member.

23. The pressurized surgical instrument recited in claim 1, wherein the pressure delivery system includes a collar in fluid communication with the elongate tubular member through a plurality of ports formed in the collar.

* * * * *

UNITED STATES PATENT AND TRADEMARK OFFICE
CERTIFICATE OF CORRECTION

PATENT NO. : 9,610,412 B2  Page 1 of 1
APPLICATION NO. : 13/020354
DATED : April 4, 2017
INVENTOR(S) : Zemlok et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 930 days.

Signed and Sealed this
Twenty-fifth Day of September, 2018

Andrei Iancu
*Director of the United States Patent and Trademark Office*